United States Patent [19]

Bradshaw

[11] Patent Number: 4,683,752
[45] Date of Patent: Aug. 4, 1987

[54] ULTRASONIC PROBE

[75] Inventor: Leslie Bradshaw, Abingdon, England

[73] Assignee: United Kingdom Atomic Energy Authority, London, England

[21] Appl. No.: 750,471

[22] Filed: Jul. 1, 1985

[30] Foreign Application Priority Data

Jul. 4, 1984 [GB] United Kingdom ................. 8417028

[51] Int. Cl.⁴ ............................................. G01N 29/00
[52] U.S. Cl. ....................................... 73/642; 73/629; 73/290 V; 73/32 A
[58] Field of Search .................. 73/290 V, 32 A, 629, 73/642

[56] References Cited

U.S. PATENT DOCUMENTS 4,509,360 4/1985 Erwin et al. .......................... 73/642
4,565,088 1/1986 Crambes ........................... 73/290 V Primary Examiner—Howard A. Birmiel
Attorney, Agent, or Firm—William R. Hinds

[57] ABSTRACT

An ultrasonic probe for measuring the velocity of sound in a liquid consists of a tube (12), closed at its lower end, and arranged to extend into the liquid, a reflector (20) alongside the tube but spaced away from it, and a source (30) of ultrasonic waves in the tube. The source is arranged so as to cause an ultrasonic beam to propagate through the tube wall (16), to traverse the liquid occupying the space between the tube (12) and the reflector (20), and to be reflected back. The source (30) can be scanned along the length of the tube to ascertain the variation of liquid properties, the position of the liquid surface, and the presence of emulsion layers and precipitates. The wall of the tube through which the ultrasonic beam emerges may be plano-concave in cross-section to enhance the ultrasonic beam intensity in the liquid.

8 Claims, 4 Drawing Figures

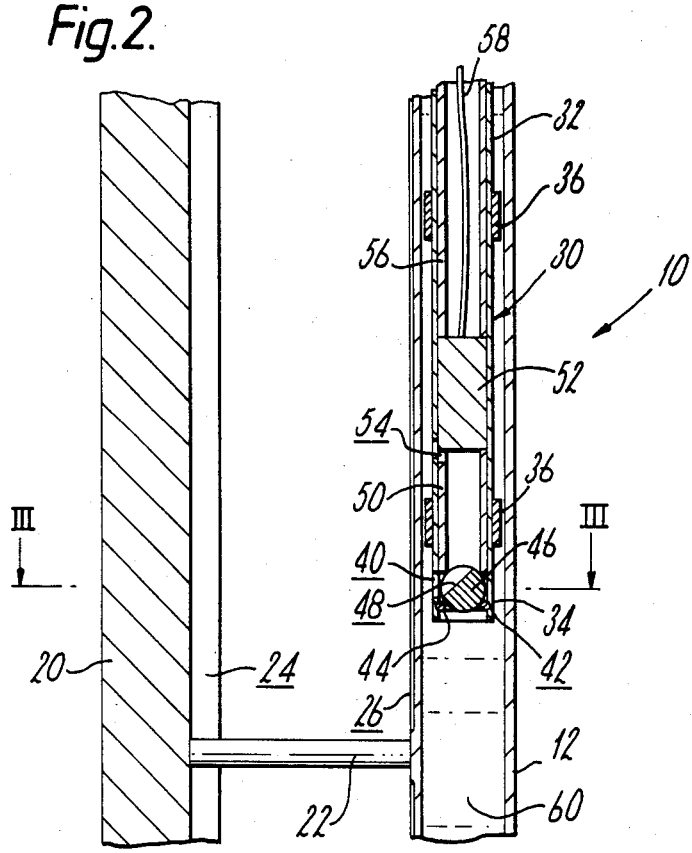

ULTRASONIC PROBE

The present invention relates to an ultrasonic probe, suitable for determining, for example, the position of a liquid level or of liquid interfaces in a storage tank, or for determining a property of a liquid.

British Pat. No. 2 084 732B describes an ultrasonic probe comprising a tube closed at its lower end and arranged to be dipped into a liquid in a tank. Extending coaxially from the closed end is a solid member through which is defined an aperture extending transverse to the tube axis so as to be occupied by the liquid. A transducer within the tube abuts the closed end and is arranged to cause ultrasonic waves to propagate in the solid member and so to traverse the aperture, and from the time taken for an ultrasonic signal to traverse the aperture a property of the liquid may be determined. Where it is desired to determine the property of the liquid at different depths in the liquid the entire probe must be moved vertically, which is inconvenient if the tank for the liquid is sealed from the surroundings, as the tube must be slid through a sealing gland. Furthermore if the tank contains any sludge or sediments these may settle out on the lower surface of the aperture, and prevent transmission of ultrasonic signals.

According to the present invention there is provided an ultrasonic probe for determining a property of a liquid, the probe comprising a tube closed at one end, an ultrasonic transducer assembly within the tube traversable along at least a portion of the length of the tube and arranged to transmit a beam of ultrasound through part of the wall of the tube, and a reflector extending parallel to the tube along the said portion of the tube, spaced apart from the tube so as to define between the tube and the reflector a gap, so that in use the gap is occupied by the liquid and the ultrasound propagates across the gap and is reflected back to the tube by the reflector the part of the wall through which the ultrasound propagates being plano-concave in transverse section, with a plane surface on the inside surface of the tube and a cylindrically-concave surface on the outside surface of tube, so as to focus the ultrasound in the gap.

Such a probe may be fixed in position in a tank for containing a liquid; measurement of a property of the liquid at different levels may be achieved by traversing the transducer assembly while leaving the tube stationary.

Preferably the reflector is of curved, part-cylindrical form, and may be defined by an open-ended tubular member attached alongside the tube.

Where it is desired to measure properties of a liquid mixture prone to form an emulsion, such as a paraffin/water mixture, the reflector is preferably defined by an open-ended tubular member attached alongside the tube, the wall of the open-ended tubular member defining a narrow axial slot, or a number of axial slots, of width about 1 mm. Within this open-ended tubular member the two components of the emulsion tend to separate into distinct layers, leaving only a thin layer of emulsion.

The transducer assembly desirably comprises a transducer arranged to transmit a beam of ultrasound along the longitudinal axis of the tube, and a reflecting surface within the tube held at a fixed distance from the transducer to deflect the beam through the wall of the tube. The reflecting surface may be plane or curved; in the preferred embodiment it is defined by a plane surface cut into a ball mounted in the tube.

The invention also provides a method utilizing such a probe for measuring properties of a liquid at a plurality of location within the liquid.

The invention will now be described by way of example only and with reference to the accompanying drawings in which:

FIG. 2 shows a longitudinal sectional view of the assembled probe of FIG. 1;

FIG. 3 shows a sectional view on the line III—III of FIG. 2; and

FIG. 4 shows a view equivalent to FIG. 3 of an alternative ultrasonic probe.

Figure 1:
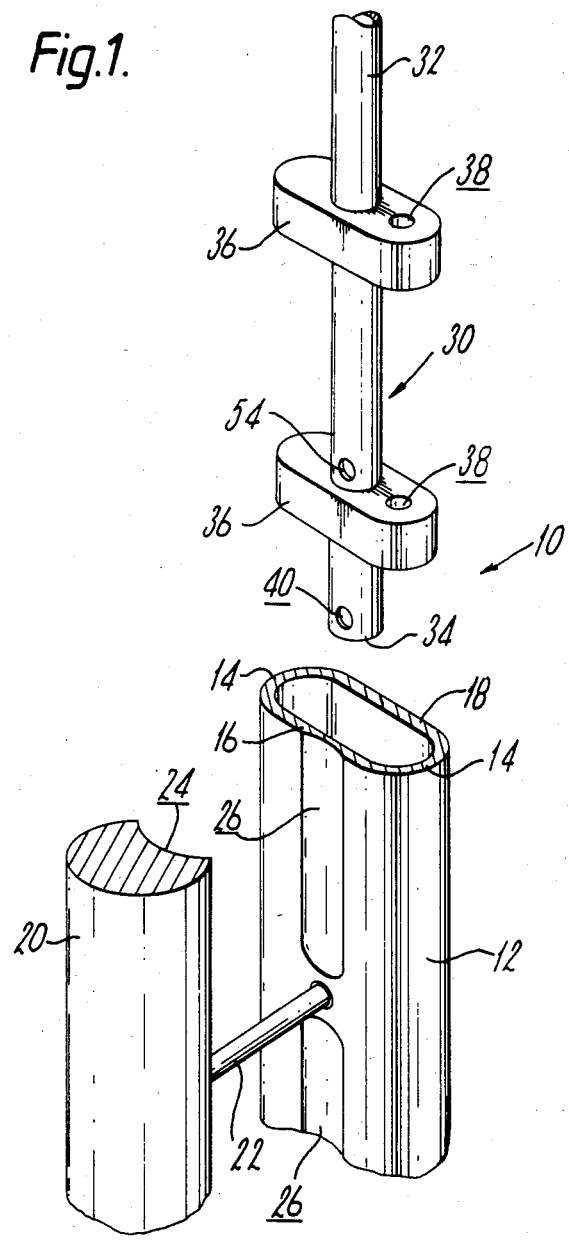
FIG. 1 shows an exploded perspective view of an ultrasonic probe.

Referring to FIG. 1, an ultrasonic probe 10 comprises a stainless steel tube 12 of squashed circular shape in transverse section having two curved wall portions 14 joined by flat wall portions 16, 18, and a stainless steel reflector bar 20 extending parallel to the longitudinal axis of the tube 12. The bar 20 is connected rigidly to the tube 12 and spaced apart from it by rods 22 (only one is shown) at intervals along the length of the bar 20, the ends of each rod 22 being welded respectively to the bar 20 and to the flat wall portion 16 of the tube 12. Part cylindrical grooves 24 and 26 are defined on the opposed faces of the bar 20 and of the flat wall portion 16, the groove surfaces 24 and 26 lying on a common cylinder.

The tube 12 is closed at its lower end and open at its upper end. A transducer assembly 30 locates within the tube 12 and is slidable along the length of the tube 12. The transducer assembly 30 comprises a cylindrical tube 32 near the lower end 34 of which are attached two spaced apart guide members 36 of substantially same cross-sectional shape and size as the inside of the tube 12. The guide members 36 ensure that the tube 32 has a constant orientation relative to the tube 12. Vent channels 38 are provided through the guide members 36 through which water can readily flow. Near the lower end 34 is a hole 40 in the wall of the tube 32 through which in operation of the probe 10 emerges an ultrasonic beam so as to be incident onto the plane inside surface of the flat wall portion 16 along a normal to the surface, and to emerge through the concavely curved surface of the groove 26.

Referring to FIG. 2, the lower end 34 of the tube 32 has an internal groove 42 in which is fitted a ring 44 of round-section wire. Resting on the ring 44 is a ball 46 with a groove defining a plane reflecting surface 48 adjacent to the hole 40. Above the ball 46 is a short tube member 50 a sliding fit within the tube 32, which spaces the ball 46 apart from a cylindrical transducer 52. Adjacent to the lower face of the transducer 52 is an air vent hole 54 through both the tube member 50 and the tube 32. Above the transducer 52 is a second tube member 56 a sliding fit within the tube 32 and which extends to the upper end of the tube 32. Electrical contact to the transducer 52 is provided by a cable 58 extending within the tube member 56. The tube 12, and hence the portion of the tube 32 below the transducer 52, is filled with distilled water 60 as a coupling liquid.

After assembly of the components within the tube 32 the orientation of the ball 46 is adjusted until the ultrasonic beam from the transducer 52 (when immersed in water) emerges through the hole 40 so as to be incident along a normal onto the inside plane surface of the flat wall portion 16 (see FIG. 3). The ball 46 is then clamped in position between the ring 44 and the tube member 50, by an axial force exerted on the upper end of the second tube member 56.

The probe 10 is installed in a storage tank (not shown) for liquids, the tube 12 being sealed through the top of the tank and extending vertically to the bottom of the tank. The bar 20 extends alongside the tube 12 from the bottom of the tank to the height of the highest expected liquid surface. The gap 62 (see FIG. 3) between the tube 12 and the bar 20 is thus filled by the liquid in the tank, or by gas or vapour above the liquid surface. The transducer assembly 30 is traversable along the length of the tube 12, but since the tube 12 is sealed at its lower end the assembly 30 does not come into physical contact with the tank contents.

In operation of the probe 10 the transducer 52 is operated in a pulse-echo mode to produce ultrasonic waves with a frequency of 10 MHz. The ultrasonic waves propagate through the distilled water 60 along the tube member 50, and are reflected by the reflecting surface 48 onto the inside surface of the flat wall portion 16. The wall portion 16, having a plane inside surface and a concave outer surface (i.e. groove 26), acts as a plano-concave lens and converges the ultrasonic waves to a focus near the centre of the circle defined by the grooves 26 and 24. The ultrasonic waves thus propagate through the liquid occupying the gap 62, and are reflected back by the curved surface of the groove 24, to pass back through the wall portion 16 into the tube 12 and so back to the transducer 52. The time taken for the echo to return to the transducer 52 after emission of the pulse is twice the propagation time within the tube 12 (which is a constant) plus twice the propagation time across the gap 62. The width of the gap 62 is a constant, so the velocity of sound in the liquid occupying the gap 62 can readily be determined. However if the gap 62 is occupied by an emulsion or sludge which is opaque to ultrasound, or if the ball 46 is above the liquid level in the tank, then no echo signal will be received. Thus, by scanning the transducer assembly 30 along the tube 12, liquid levels, and liquid interfaces, variations of concentration of a dissolved material, and positions of any sludge or emulsion layers within the tank can readily be determined.

Referring now to FIG. 4, a cross-sectional view is shown of an ultrasonic probe 80 similar in many respects to that of FIG. 1, identical components being referred to by the same reference numbers. The probe 80 comprises a tube 82 of D-shaped cross-section with a flat wall portion 84 and a curved wall portion 86, sealed at its lower end, and filled with distilled water 60 as a couplant liquid. A transducer assembly 88 is located within the tube 82 and is slidable along its length, differing from the transducer assembly 30 only in the shape and size of the two guide members (not shown), which are of D-shaped cross-section. The assembly 88 is arranged so that, in operation, an ultrasonic beam is incident onto the plane surface of the flat wall portion 84 along a normal. Adjacent to the tube 82 is an open-ended cylindrical chamber 90 of circular internal shape in cross-section, integral with the tube 82. The wall portion 84 is common to both tube 82 and the chamber 90, being plane on one face and curved concavely on the opposite face. If the chamber 90 is occupied by a liquid then the ultrasonic beam will be focussed by the plano-concave shape of the wall portion 84, and will traverse the chamber along a diametral path, being reflected back by the concavely curved wall of the opposite side of the chamber 90.

Slots 92 are defined through the wall of the chamber 90, extending parallel to the longitudinal axis, and diametrically opposite each other so as to lie in a plane substantially perpendicular to the ultrasonic beam. Each slot 92 is 100 mm long and 1 mm wide, and a line of the slots 92 extends the entire length of the chamber 90, the ends of colinear adjacent slots being 3 mm apart.

The probe 80 is installed in a settling tank (not shown) into which flows a mixture of water and kerosene. The tube 82 is sealed through the top of the tank and extends vertically to next to the bottom. The open-ended chamber 90 extends from next to the bottom to the height of the highest expected liquid surface. The transducer assembly 88 is traversable along the tube 82 beside the chamber 90 but is not in physical contact with the contents of the tank.

Operation of the probe 80 is substantially the same as that of the probe 10. The chamber 90 is occupied by the liquids in the tank, and by scanning the transducer assembly 88 the velocity of sound in the liquid at the level of the ball 46, or the presence of air or opaque emulsion, can be determined. The mixture of water and kerosene tends to form an emulsion, which would prevent measurement of the concentration of a dissolved material in either of the two liquids. However the narrow slots 92 tend to act as a barrier to the entry of emulsion while permitting the entry of the separated liquids. Hence the emulsion layer within the chamber 90 is thinner than that in the tank, so making possible the measurement of velocity of sound in clear liquids above and below the emulsion.

Although the reflecting surface 48 has been described as being plane it will be appreciated that it may alternatively be curved so as to focus or diverge the ultrasonic beam in a desired manner. Furthermore although the chamber 90 has been described as having two lines of axially extending slots 92, it will be appreciated that the slots 92 may be staggered so that adjacent slots 92 overlap each other. It will also be understood that although the probe 10 has been described as producing ultrasonic waves of frequency 10 MHz, other frequencies may be used depending on the dimensions of the equipment and on the properties of the liquids being scanned.

I claim:

1. An ultrasonic probe for determining a property of a liquid, the probe comprising a tube closed at one end, an ultrasonic transducer assembly within the tube, traversable along at least a portion of the length of the tube and arranged to transmit a beam of ultrasound through part of the wall of the tube, and a reflector extending parallel to the tube along the said portion of the tube, spaced apart from the tube so as to define between the tube and the reflector a gap, so that in use the gap is occupied by the liquid and the ultrasound propagates across the gap and is reflected back to the tube by the reflector, the part of the wall through which the ultrasound propagates being plano-concave in transverse section, with a plane surface on the inside surface of the tube and a cylindrically-concave surface on the outside surface of the tube, so as to focus the ultrasound in the gap.

2. An ultrasonic probe as claimed in claim 1 wherein the reflector is of curved, part-cylindrical form.

3. An ultrasonic probe as claimed in claim 2 wherein the reflector is defined by an open-ended tubular member attached alongside the tube.

4. An ultrasonic probe as claimed in claim 3 wherein the tubular member defines at least one axial slot of width about 1 mm.

5. An ultrasonic probe as claimed in claim 2 wherein the outer surface of the part of the wall through which the ultrasound propagates into the gap is cylindrically concave, defining a common cylinder to that defined by the reflector.

6. An ultrasonic probe as claimed in claim 1 wherein the transducer assembly comprises a transducer arranged to transmit a beam of ultrasound along the longitudinal axis of the tube, and a reflecting surface within the tube and movable with and at a fixed distance from the transducer to deflect the beam through the wall of the tube.

7. An ultrasonic probe as claimed in claim 6, wherein the reflecting surface is defined by a plane surface cut into a ball mounted in the tube.

8. A method for determining values of a property of a liquid at a plurality of locations within the liquid comprising traversing an ultrasonic transducer assembly along at least a portion of the length of a tube closed at one end, with a reflector extending parallel to the tube along the said portion of the tube, spaced apart from the tube so as to define between the tube and the reflector a gap which is occupied by the liquid, part of the wall of the tube nearest the reflector being plano-concave in transverse section, with a plane surface on the inside surface of the tube and a cylindrically-concave surface on the outside surface of the tube, energising the transducer assembly to cause ultrasound to propagate through the plano-convave part of the wall of the tube so as to propagate across the gap and be reflected back to the tube by the reflector, and observing the reflected signals obtained at the said locations.

* * * * *